US011446767B2

(12) United States Patent
Lausch et al.

(10) Patent No.: US 11,446,767 B2
(45) Date of Patent: Sep. 20, 2022

(54) COMPOSITE BODY HAVING AT LEAST ONE FUNCTIONAL COMPONENT, AND A METHOD OF PRODUCING SAID COMPOSITE BODY

(71) Applicant: Fraunhofer-Gesellschaft zur Foerderung der angewandten Forschung e.V., Munich (DE)

(72) Inventors: Holger Lausch, Leipzig (DE); Mathias Herrmann, Coswig (DE); Bernd Gronde, Schleifreisen (DE); Thomas Toeppel, Bischofswerda (DE); Romy Petters, Dresden (DE); Christian Rotsch, Dresden (DE)

(73) Assignee: FRAUNHOFER-GESELLSCHAFT ZUR FOERDERUNG DER ANGEWANDTEN FORSCHUNG E. V., Munich (DE)

( * ) Notice: Subject to any disclaimer, the term of this patent is extended or adjusted under 35 U.S.C. 154(b) by 1212 days.

(21) Appl. No.: 15/763,133

(22) PCT Filed: Sep. 27, 2016

(86) PCT No.: PCT/DE2016/100450
§ 371 (c)(1),
(2) Date: Nov. 15, 2018

(87) PCT Pub. No.: WO2017/054799
PCT Pub. Date: Apr. 6, 2017

(65) Prior Publication Data
US 2019/0061058 A1 Feb. 28, 2019

(30) Foreign Application Priority Data
Sep. 28, 2015 (DE) .................. 102015116409.4

(51) Int. Cl.
*B23K 26/354* (2014.01)
*B22F 7/08* (2006.01)
(Continued)

(52) U.S. Cl.
CPC .......... *B23K 26/354* (2015.10); *A61F 2/3094* (2013.01); *A61F 2/36* (2013.01);
(Continued)

(58) Field of Classification Search
CPC ... C23C 4/08; C23C 4/134; B22F 5/10; B22F 10/20; A61F 2002/30985;
(Continued)

(56) References Cited

U.S. PATENT DOCUMENTS 5,996,219 A 12/1999 Golnas et al.
6,215,093 B1 4/2001 Weiners et al.
(Continued)

FOREIGN PATENT DOCUMENTS

DE 102011105044 A1 12/2012
DE 102014201306 A1 7/2015
WO 9824574 A1 6/1998

*Primary Examiner* — Jimmy Chou
(74) *Attorney, Agent, or Firm* — Abel Schillinger, LLP

(57) ABSTRACT

The invention relates to a composite body, wherein at least one functional component is integrated into a shaped product, and to a method for producing the same. The shaped product can especially be an implant, a prosthesis, an industrial component or a multifunctionally useful sensor platform for the monitoring of materials, components and/or structural systems.

20 Claims, 13 Drawing Sheets

(51) Int. Cl.

| | |
|---|---|
| *G01D 11/24* | (2006.01) |
| *B33Y 80/00* | (2015.01) |
| *B33Y 10/00* | (2015.01) |
| *B33Y 40/00* | (2020.01) |
| *A61F 2/30* | (2006.01) |
| *A61F 2/36* | (2006.01) |
| *B22F 10/20* | (2021.01) |
| *B23K 26/34* | (2014.01) |
| *A61F 2/46* | (2006.01) |
| *B22F 5/10* | (2006.01) |
| *A61F 2/48* | (2006.01) |
| *C23C 4/134* | (2016.01) |
| *C23C 4/08* | (2016.01) |

(52) U.S. Cl.
CPC ............... *B22F 7/08* (2013.01); *B22F 10/20* (2021.01); *B23K 26/34* (2013.01); *B33Y 10/00* (2014.12); *B33Y 40/00* (2014.12); *B33Y 80/00* (2014.12); *G01D 11/245* (2013.01); *A61F 2/4657* (2013.01); *A61F 2/482* (2021.08); *A61F 2002/30087* (2013.01); *A61F 2002/30593* (2013.01); *A61F 2002/30985* (2013.01); *B22F 5/10* (2013.01); *C23C 4/08* (2013.01); *C23C 4/134* (2016.01); *Y02P 10/25* (2015.11)

(58) Field of Classification Search
CPC .. A61F 2002/30593; A61F 2002/30087; A61F 2/4657; A61F 2/36; A61F 2/3094; Y02P 10/25; B23K 26/34; B23K 26/354; B33Y 80/00; B33Y 40/00; B33Y 10/00
USPC .................................................. 219/121.66
See application file for complete search history.

(56) References Cited

U.S. PATENT DOCUMENTS

| | | | |
|---|---|---|---|
| 9,668,392 B2 | 5/2017 | Rauschenbach et al. | |
| 2007/0177362 A1 | 8/2007 | Fortson | |
| 2009/0142209 A1* | 6/2009 | Hirata | H01L 41/257 417/413.2 |
| 2010/0059496 A1* | 3/2010 | Rena | F02P 19/02 219/270 |
| 2010/0192806 A1* | 8/2010 | Heugel | B22F 10/70 106/286.1 |
| 2012/0209394 A1* | 8/2012 | Bojarski | A61B 17/157 623/20.32 |
| 2014/0165381 A1* | 6/2014 | Rauschenbach | H01L 41/23 29/592.1 |
| 2015/0144386 A1 | 5/2015 | Kim | |
| 2015/0188024 A1* | 7/2015 | Ishigami | H01L 41/0475 419/10 |
| 2015/0196971 A1* | 7/2015 | Schneider | B23P 15/006 219/76.14 |
| 2015/0359638 A1* | 12/2015 | Khowaylo | A61L 27/045 623/18.11 |
| 2015/0367448 A1* | 12/2015 | Buller | B29C 64/171 219/74 |
| 2016/0083833 A1* | 3/2016 | Rickerby | C23C 4/11 427/454 |
| 2016/0184606 A1* | 6/2016 | Flühs | A61N 5/1017 600/7 |
| 2016/0242877 A1* | 8/2016 | Bernhard | A61C 13/0018 |
| 2016/0258256 A1* | 9/2016 | Nguyen | E21B 34/06 |
| 2018/0125365 A1* | 5/2018 | Hunter | A61B 5/01 |
| 2021/0220915 A1* | 7/2021 | De Pasquale | B22F 10/70 |

* cited by examiner 7  6  3  3.1  1   4   8

A - A 3.1  3     8              3.1

COMPOSITE BODY HAVING AT LEAST ONE FUNCTIONAL COMPONENT, AND A METHOD OF PRODUCING SAID COMPOSITE BODY

BACKGROUND OF THE INVENTION

Field of the Invention

The invention relates to a composite body, in which at least one functional component is integrated into a shaped product, and to a method for producing the same. Here, the shaped product can be, in particular, an implant, a prosthesis, an industrial component or a multifunctionally useful sensor platform for the monitoring of materials, components and/or structural systems.

Discussion of Background Information

Additive (generative) manufacturing methods have made enormous progress in the last three decades as regards the variety of materials, productivity, accuracy and material properties. For this reason, generative methods are increasingly also being used for the series production of complex components. Particularly powder-based methods, such as laser beam melting for metallic materials, are showing the greatest potential for enabling geometrically complex workpieces and tools to be produced in series-identical materials with series-identical properties to those of conventional manufacturing methods, e.g. milling or casting.

A shaped body is produced additively by solidification in layers at selected locations by means of a locally defined energy input into powdered fusible materials. Here, the energy is input by means of an energy beam, in particular a laser beam or electron beam. Known method names for this are "selective laser melting (SLM)", "laser melting", "laser forming", "laserCUSING" or "direct metal laser sintering (DMLS)", and "electron beam melting (EBM)". This method is summarized as beam melting below.

In beam melting systems, three-dimensional bodies can be produced by the layer buildup principle, wherein individual powder layers are melted successively at selected locations by an energy input, e.g. by laser beam, and solidify to form a solid shaped body. In this case, the material powder, which is made available by means of a powder supply chamber for example, can be distributed over a construction platform in a process chamber by means of a sliding device in a procedure in which the sliding device is moved horizontally in order in this way to apply a layer of material powder, typically 20 µm to 150 µm thick, in a defined programmable way. One or more laser beams then selectively scan those regions of the applied powder layer which are to be melted, by means of fiber or diode lasers for example. Upon conclusion of the local melting of the layer, the construction platform of the process chamber is lowered by the selected layer thickness to enable another layer to be applied, thus allowing the workpiece to be produced in layers.

A device of this kind and a method for additive production of a workpiece/shaped body by laser beam melting of a powdered material are known from WO 98/24574 A1.

In the case of such a possibility for the production of shaped bodies of this kind, which is admittedly very flexible, the beam melting generally gives rise to very high temperatures.

If the intention is to integrate further elements into or onto the shaped body, production of the composite in one manufacturing process is virtually impossible.

It is therefore the object of the invention to specify ways of configuring and producing a composite body with which at least one functional component can be integrated into a shaped body, which is produced generatively from a metallic powder by beam melting, without the elevated temperatures leading to impairment of the functionality of the respective functional component.

SUMMARY OF THE INVENTION

The object is achieved by a composite body having at least one functional component and one shaped body by virtue of the fact that the at least one functional component is arranged so as to be connected to a metallic or ceramic support structure having at least one contour element, and the at least one functional component is surrounded at least in some region or regions by at least one thermally insulating layer composed of a ceramic material and at least one thermally conductive layer lying above the latter and composed of a metal or metal oxide. Here, the shaped body, which is produced generatively by beam melting of a metal powder, completely surrounds the at least one functional component and the support structure with the at least one contour element. At least one of the at least one contour elements has a material connection to the shaped body.

The composite body is likewise characterized by the fact that the architecture and building up of the functional component to give the shaped body are configured in such a way that, on the one hand, an energy flow and transfer from outside the shaped body to the functional component are possible and, on the other hand, an energy flow and energy transfer between the functional component and the shaped body while preserving functionality are possible generally and, more particularly, after the material integration by means of beam melting, including or excluding thermal and/or mechanical aftertreatment processes, in particular joining and compaction processes. On the one hand, the aftertreatment processes ensure separation of the functional component in terms of materials, chemistry and corrosion from the medium surrounding the shaped body or from influences and, on the other hand, ensure the diffusion of chemical and material constituents of the functional component through the shaped body to the environment surrounding the shaped body. This must be assured even in the case of a mechanical or traumatic deformation of the shaped body. This leads to the necessity of thermal and/or mechanical aftertreatment of the shaped body or of an appropriate mode of construction/architecture of the shaped body. As a result, the functional component is hermetically/leaktightly enclosed in the shaped body, thus ensuring chemical and mechanical protection (e.g. protection from pressure or wear) for the functional component from environmental influences outside the composite body. Moreover, the shaped body also forms a thermal protection of the functional components from external environmental influences around the functional component. Conversely, the shaped body can also act as a chemical and/or mechanical and/or thermal barrier in order to protect the environment surrounding the composite body from chemical and/or mechanical and/or thermal influences from the functional component.

In addition to the conventional positive and/or material integration of a functional component into a shaped body, embodiments are possible whose primary aim is interaction between the two elements or with the environment or whose aim is the material and/or positive connection of the functional component, e.g. a piezoelectric actuator, or the provision of a counterbearing or of a clamping device for the latter, if monolithic positive and material embedding is not necessary but instead hinders transmission of vibration. The functional component can be integrated into the shaped body in such a way that, on the one hand, it can be moved in at least one dimension relative to the shaped body and, on the other hand, has unfilled volumes (e.g. air, protective gas or unmelted powder material).

The integrative connection must be configured in such a way that a gradient transfer or gradient compensation to form a physical equilibrium in the form of an energy transfer is possible between the functional component and the shaped body. In this way, the coupling in of mechanical energy in the form of vibrations and differences in internal stress, which are converted from structural noise to spatial noise only at the surface of the shaped body or of a defined area for example, can take place. By providing at least one geometrical degree of freedom of the functional component and of a force transmission corridor to the shaped body, which is connected positively, nonpositively and materially by means of a tongue and groove joint by way of beam melting for example, a defined gradient transfer in the abovementioned sense is possible. In the case of the coupling in of thermal energy, monolithic positive and material embedding is likewise not necessary per se. The thermal energy arising in a functional component due to conversion, for example, can be transmitted in such a way, by means of "thermotunnels" with surrounding thermal insulation or air or protective gas (thermoscanning effect) or unmelted powder in the shaped body, as far as other functional components in the shaped body and/or at the surface of the shaped body so as to form a thermal equilibrium, that there is no heating or only a little heating of the overall shaped body. This likewise applies to the coupling in of electric/electromagnetic energy, including remanence and translational forces from the converting functional component to topical functional regions within and/or on the surface of the shaped body via electrically insulated, e.g. ceramically sheathed, electric flux sections. In all cases mentioned, an energy equilibrium between the functional component and topical areas in or on the surface of the shaped body in the sense of an energy equilibrium is produced by means of thermally, electrically or mechanically sheathed transmitters constrained by degrees of freedom. The other functional components in the shaped body or at the surface of the shaped body and/or topical areas of the shaped body itself form a kind of consumer or load relative to a primary energy-converting and signal-generating functional component. In each case, the primary functional component influences the shaped body or other secondary functional components and the environment surrounding the shaped body. This also applies in reverse, thus enabling an actuator-type functional component to become a sensor-type functional component.

The object is furthermore achieved by a method for producing a composite body by virtue of the fact that, first of all, at least one functional component is connected to a metallic or ceramic support structure, the at least one functional component is then provided at least in some region or regions with at least one thermally insulating surrounding layer composed of a ceramic material by means of thermal spraying, a thermally conductive layer composed of a metal or metal oxide is then applied on top, likewise by means of thermal spraying, a partial body having at least one beam melting zone and an aperture for receiving the unit produced thus far is then produced generatively and in layers by beam melting a metal powder, the unit produced thus far is then inserted positively and/or nonpositively into the aperture in the partial body, wherein the support structure is connected materially, by means of the beam melting zone, to the partial body, indirectly or directly via contour elements and/or via bosses, and, finally, the partial body is covered over generatively or in layers with at least one further partial body, likewise by beam melting a metal powder, thus giving rise to a monolithic shaped body.

In this case, the energy beam should be operated in such a way and the focal spot thereof moved in such a way during the beam melting process that a maximum temperature specific to the respective functional component is not exceeded during the production of the shaped body. The energy density in the focal spot of the energy beam, the feed rate of the focal spot, the spacing between melting tracks, the respective layer thickness of the powder layers and/or the irradiation pattern can be influenced in such a way that the specific maximum temperature is not reached at the functional component. It is advantageous if work is carried out with an energy input reduced by at least 10%, preferably by at least 20%, in the regions adjoining the functional component.

The beam melting process is advantageously carried out in such a way that, for example, the mechanical vibration or stress changes can be ensured by means of appropriate geometrical degrees of freedom from the energy-absorbing and converting functional component to the shaped body.

A cavity can simultaneously be an integration space within the shaped body with corresponding material connection points (melting zones or integration zones). Accordingly, the support structure is equipped with one or more contour elements.

The conscious abandonment of positive monolithic sheathing of the functional component with the surrounding shaped body thus creates unfilled or not tightly packed cavities or interspaces which make it possible to achieve an additional thermal insulating effect. Through the choice of the design and production steps for the shaped body, e.g. the choice of an arch-forming sheath, stable positive connection regions and simultaneously thermally insulating regions can be formed. The design of the arrangement between the integrating melting zone on the shaped body and the integrating melting zone on the support structure of the functional component can be configured in such a way as a connection interface that the thermal energy input in the region of the connection interface is guided away from the thermally more sensitive functional component toward the more thermally conductive connection point of the shaped body inasmuch as the proportion of the material of the shaped body at the connection interface is greater than in the region of the functional component. This effect can also be increased if the geometrical configuration of the support structure in the region of the connection interface with the shaped body, e.g. at the surface, has a lower heat conduction and/or storage coefficient than in the interior of the support structure, i.e. the support structure has a corresponding gradient. If the support structure is likewise produced separately by beam melting, the microstructure in the region of the future connection interface can be configured in such a way that a positive, nonpositive and material connection are possible. During beam melting, the microstructures (crystal shape, type of material, alloy) should be the same to an adequate extent on both sides of the beam melting zone, i.e. in the region of the contour elements of the functional component and the shaped body. At the same time, the connection interface region of the support structure can have an even lower thermal conductivity than the remaining part of the support structure of the functional component, which accommodates the thermally sensitive component parts of the functional component. This can also be achieved, as described above, if the support structure is composed of ceramic, for example, and only the interface region is metallically coated, this being possible by means of thermal spraying, for example.

The design aspects also require adaptations in the production sequence in the beam melting process. In beam melting, the quality of the positive, nonpositive and material joint in the connection region depends significantly on the process management. Uniform powder application for the layers to be built up at the connection interface but also at the unfilled or not tightly packed cavities or interspaces with respect to the functional component should be maintained. If such an area (volume) is not to be filled with powder or filled by means of a manipulator with a thermally insulating mixture of powder or spheres (granules, particles etc.) in order, for example, to obtain better thermal insulation or to protect the functional component from reaching a maximum permissible temperature, e.g. the melting point, the volume energy input in the region in which melting of the powder or of the exposed functional component surface is not desired can be reduced locally in a defined manner. In this region, however, the volume energy input should not be reduced completely in order to ensure that stress gradients between melted and unmelted regions of the metal powder do not arise during the melting process. The limit to the lowering of the volume energy input is always the preservation of the functioning of the interface (positive, nonpositive and material connection) and the static preservation of the functioning of the shaped body and of the embedded functional component (i.e. as a result, the lowering of the volume energy input also depends on the wall thicknesses used, on the material and on the design of the shaped body). Locally defined process control of the volume energy input is advantageous, e.g. of the laser power, feed rate, spacing of the welding tracks, irradiation pattern and/or layer thickness, which, on the one hand, allows locally defined melting of the powder and, on the other hand, allows locally defined stress-reducing heat treatment of that region on the functional component surface which surrounds the molten pool. In general, this can be achieved in a targeted manner by means of the system and process control. The locally defined process control in the abovementioned sense should not only be appropriate two dimensionally in the respective current powder layouts to be melted but it should furthermore also be modifiable in a defined way by means of the variation of the volume energy input in the previous and following powder layers. This stress-reducing heat treatment includes process control, for example, wherein the metal powder applied and/or the already melted layers thereunder are preheated before the beam melting of the newly applied metal powder layer. This is particularly important if the already melted layers form inwardly-open frames, for example, and the beam melting process takes place diagonally across the frame parts, which are generally connected thermally to a different material thereunder. In this way it is possible to ensure that an open frame is closed at the top and the bottom. The preheating of the already melted layer can take place before or after the application of the new metal powder layer. By monitoring the volume energy input and detecting the actual melting zone and the degree of integration resulting therefrom, it is possible, in turn, to adjust the volume energy input in a self-regulating manner in real time and in a locally defined manner. For such real-time monitoring and control of the beam melting process, it is particularly advantageous here to use two measurement methods, to be employed in parallel, involving different physical measurement principles that do not influence one another, e.g. optical and acoustic detection and characterization of the running melting process.

Actuators and/or energy converter elements, especially electric, electromagnetic, mechano-acoustic, kinetic, thermal and other converter systems can preferably be used as functional components.

For the integration of a functional component with a surrounding shaped body with different functionalities, a varying sequence of successive process steps is advantageous. Thus, for example, it is advantageous to divide the additive production process into at least two steps in the case of integration of a functional component into a shaped body, e.g. an implant or a prosthesis or an industrial component or a multifunctionally useful sensor platform for the monitoring of materials, components and/or structural systems, thus enabling the shaped body to be manufactured from a plurality of partial bodies that can be produced separately. The manufacturing process for the shaped body can be carried out additively without interruption by means of beam melting until the accommodation space for a functional component or components with a support structure and the connection interface, e.g. a gap, groove, slot etc., has been built up and the actual positive, nonpositive and material connection can be made. If the functional component has already been thermally protected by a preceding separate embedding process, the shaped body can be continued by means of beam melting after the connection of the functional component and of a partial body, and at least one further partial body produced by means of beam melting can be connected materially to the partial body which is already connected to the functional component via the support structure. The material connection can be achieved during beam melting. However, brazing, welding or forging are also possible. If the embedding of the functional component in the shaped body is accomplished through the production of partial bodies, partial bodies form separate semifinished products or functional units (e.g. a monolithically fully sheathed partial body). Partial bodies can be welded, brazed, cast, mechanically joined or adhesively bonded to further partial bodies or other shaped bodies, e.g. as actuators, sensors or monitoring systems.

If the functional component cannot be integrated into the interior space without projecting or must be subject to undercutting in terms of its shape, it is necessary to adapt the technology of the beam melting system. According to the invention, manipulator-type, robot-controlled material powder feed systems and three-dimensionally movable and/or rotatable production table elements should be used to receive the construction platform, and/or three-dimensionally movable laser beam guiding and shaping systems should be used. The particular advantage of the ability to guide the construction platform and/or material powder feed and/or the laser in three dimensions is that, in this way, complex shaped bodies, even those with undercuts, can be formed and the functional component can be embedded or surrounded more effectively. With such a possibility of 3-D guidance of the construction platform and/or material feed and/or the laser, embedding and surrounding can furthermore advantageously be carried out even with partial and/or full projection beyond the powder bed surface during beam melting, i.e. projection in the vertical direction. The integration of ceramic or metallic auxiliary and holding structures which can be inserted temporarily and removed again after the melting of a topical region can likewise also be advantageous here.

Thus, for example, the functional component can be integrated into a sleeve of the same material, likewise produced additively beforehand, and using the same method. The functional component and the sleeve can be connected to one another at individual points, linearly or over an area. It can also be advantageous here if this sleeve is pretreated separately without the functional component by thermal methods, e.g. hot isostatic pressing (HIP), in a manner which involves compaction of the material. The functional component cannot then be introduced in an absolutely positive and/or nonpositive manner into the sleeve (play, crumple zone, deformation zone) and can only be connected positively, nonpositively and/or materially by means of its connection interfaces with the shaped body. A mechanical, nonthermal post-compaction of the shaped body with the integrated functional component can be performed, this being possible, for example, by massive cold forming in order, for example, to establish a layer or material zone with optimum force absorption characteristics which protects the functional component from excessive mechanical deformation. In this way, it is possible, for example, for the shaped body to be compacted in such a way to ensure a necessary strength, stiffness and stability, after the integration of the functional component and the completion of additive production and optionally subsequent further joining processes, that the functional component is not deformed in a manner which impairs functioning. In this case, locally defined compaction in certain regions of the shaped body, e.g. at a defined distance from the connection interface, is also advantageously possible. By way of the individual mechanical properties of the separate volumes, it is possible, for example, to establish material properties in a spatial manner, with the result that, for example, load bearing regions can in this way be passed around the functional component region in a force-absorbing manner without impairing the overall stability of the shaped body and the functioning of the functional component.

For the integration of a functional component into a shaped body in the form of an implant or of a prosthesis or of an industrial component or of a multifunctionally useful sensor platform for the monitoring of materials, components and/or structural systems as an overall shaped body, it is advantageous, for example, if the shaped body is produced from at least two segmented partial bodies, which are produced additively and can be joined additively or conventionally. The individual volumes of the overall shaped body can be subjected to separate thermal and/or mechanical treatment processes before the joining process, for example, in order to be able to establish selected material properties.

It can be advantageous if the shaped body comprises at least two partial bodies which are manufactured generatively and subsequently joined together after the integration of the functional component into one of the partial bodies. This can be accomplished by means of welding or forging, for example. It can furthermore be advantageous if the shaped body comprises at least two partial bodies and, after the integration of the functional component into the first partial body, all the other partial bodies are built up generatively on the first partial body by means of beam melting until the shaped body has been produced completely. If a central partial body of a shaped body with a bilaterally open/pierced cavity for the reception of the functional component with the abovementioned connection interfaces (groove, slots, gaps etc.) on the shaped body side of the corresponding opposite connection interfaces of the support structure of the functional component (tongue, anchor etc.) is built up additively and separately, the respective additive manufacturing process can be continued after the insertion, mechanical fixing and placing thereof on the upper or lower side of the central partial body, wherein, first of all, the respective upper or lower connection interfaces of the adjoining or adjacent connection interfaces can be connected. The receptacle with the functional component can be covered partially or completely, positively, materially and/or nonpositively in segments. A positive, nonpositive and/or material connection relative to the additively produced partial body is thus possible on both sides of the functional component.

Thus, at least one contour element can be formed on the support structure. A contour complementary to the contour element(s) can be formed on the shaped body or on a partial body for the production of a shaped body, with the result that it is thereby possible to obtain at least one positive connection when the functional component with the support structure is inserted. Given appropriate dimensioning of the contour element(s) and the contour(s) in the shaped body or a partial body, a nonpositive connection in the form of a press fit can also be achieved in addition. It is very important here that the at least one contour element of the support structure of the functional component should have at least one material connection to the shaped body in order to reliably ensure the actuator and/or sensor functionality of the composite body.

One significant advantage of the invention consists in the abandonment of cover structures, screw structures or other structural fixing and prestressing steps, for example, in the additive production method if the prestressing and fixing of a piezoelectric actuator as a functional component, for example, is accomplished not directly through the configuration of the receptacle in the shaped body but through the configuration of the support structure, which it is likewise particularly advantageous to pre-produce by beam melting, for example.

It may be advantageous if the functional component is embedded in a partial body of the shaped body as a semifinished product in order subsequently to be integrated as a semifinished product/partial body into the production of the composite body.

It is possible to dispense with a support structure that has separate contour elements/interfaces if the functional component is a thermal energy converter, for example, since there is no need for a direct gradient transition between the functional component and the shaped body. In such a case, the connection interface can be of significantly larger or significantly different dimensions.

If a sleeve having raised portions and depressions situated on the surface thereof is used as the surrounding semifinished product for a functional component, for example, the connection to the shaped body can take place only in the region of raised portions. In this way, it is possible to obtain unfilled cavities with a thermal insulating character over a large area, with the result that heat energy from the functional component can pass into the surrounding shaped body and, conversely, pass from the shaped body to the functional component only with difficulty (thermoscanning effect). The same effect can also be achieved by covering over the functional component in the manner of an arch and thus forming a cavity and by the positive, nonpositive and/or material integration taking place only in the region of the connection interfaces, e.g. a tongue-groove connection (interfaces).

In order to allow function-preserving embedding of a functional component (actuator or sensor), the energy input during the beam melting process should be locally limited. Care should furthermore be taken to ensure that the temperature gradient between the regions which currently require melting and those which have already been melted and solidified is not too high in order in this way to reduce stresses. An energy input which is matched/varied with respect to location/time can likewise be advantageous. This can be appropriate, for example, in carrying out the direct covering of the functional component, i.e. covering involving a buildup on said component, or the covering over of the functional component in the manner of an arch, with the energy input of the energy beam being increased with increasing distance from the functional component and reduced in the vicinity of the functional component, for example (short distance=low energy input, large distance=high energy input). Here, the proportioning of the energy input should be chosen so that the material bond is still assured. If the material bond nevertheless requires a higher energy input, the temperature-sensitive region situated thereunder, in which a functional component is arranged, can be sheathed with a layer that provides greater heat distribution in order to distribute the heat input over a larger region in the shaped body or partial body together with the functional component and thus reduce said input in a locally defined manner. Depending on the type and mode of action of the functional component and the configuration of the surrounding shaped body, the thermal protective sheath system in the partial body with the functional component and the energy input during additive manufacture should be matched to one another. This can also be taken into account in the design by appropriately influencing the energy input during the materially bonded welding of the tongue and groove. Owing to the high proportion of the material in the outer region of the shaped body or of a partial body with the functional component, that region which performs a frame function, the majority of the thermal energy input can be transferred to this frame region and not to the functional component. Heat can thus also be dissipated, i.e. kept away from the support structure of the functional component. The process can advantageously be carried out with preheated powder and a preheated component. This can be accomplished by heating the construction platform, radiant heating, induction heating or construction chamber heating, for example.

Additional advantageous embodiments can be found in the subclaims.

In this application, "specific maximum temperature" is intended to mean that the respectively affected element is subjected at most to a temperature such that this element does not suffer any damage in terms of its functions, i.e. after the application of a temperature increase is ended, it is fully functional in accordance with its intended use.

By means of this invention, it is possible to detect a change in stress within the shaped body. For this purpose, at least one functional component with an actuator action and one functional component with a sensor action are advantageously integrated into the shaped body, wherein the at least one functional component with an actuator action excites the shaped body into vibration (structural noise) and the at least one functional component with a sensor action detects the vibrations. In this way, stress states which vary with respect to time can be detected within the shaped body. In this way, it is possible to monitor the mechanical state of the component and to predict failure of the component at an early stage.

BRIEF DESCRIPTION OF THE DRAWINGS

The invention will be explained in greater detail below by means of illustrative embodiments with the aid of drawings, in which.

DETAILED DESCRIPTION OF EMBODIMENTS OF THE INVENTION

Figure 1:
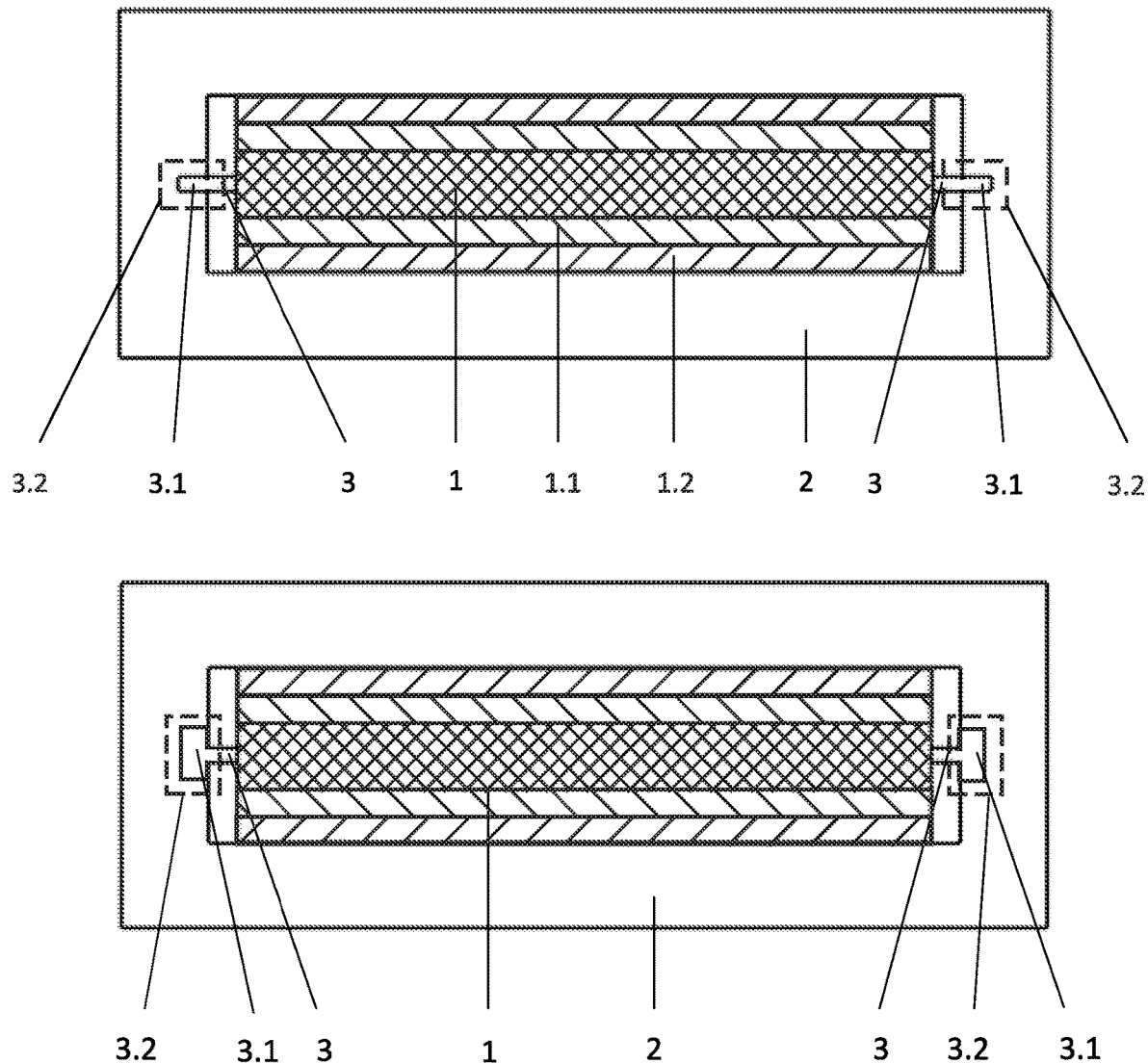
FIG. 1 shows an example of an element produced according to the invention, in which a functional component is connected positively, nonpositively and materially to a shaped body by means of a support structure, in two views.

Sectional illustrations in two views of a composite body with a functional component 1 which is connected positively and materially to a shaped body 2 in the region of contour elements 3.1 of a support structure 3 are shown in FIG. 1. The functional component 1 is surrounded by a thermally insulating layer 1.1 of ceramic material and a thermally conductive layer 1.2 of thermally conductive metal, metal alloy or metal oxide lying above the thermally insulating layer 1.1. Here, the support structure 3 is preferably formed from the same metal as the shaped body 2, which has been produced generatively in layers from metal powder by beam melting. In this case, the functional component 1 is preferably connected positively to the support structure 3, which is provided with through-openings/apertures (see FIG. 2).

The beam melting zone 3.2 marks the integration zones where the material connection between the contour elements 3.1 of the support structure 3 of the functional component 1 and the shaped body 2 is produced by beam melting.

Figure 2:
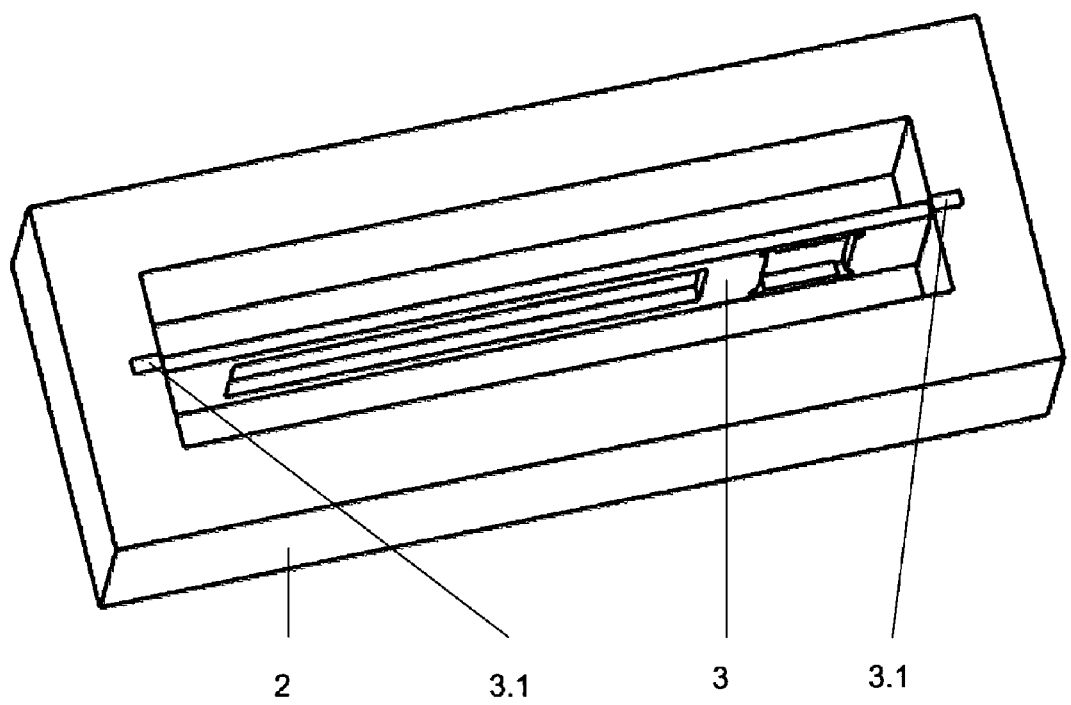
FIG. 2 shows an example of a support structure connected positively, nonpositively and materially to a shaped body, in which the functional component is not shown.

According to FIG. 2, there are contour elements 3.1 at the two opposite ends of the support structure 3, said contour elements being surrounded during generative production with the material of the shaped body 2, thus enabling a positive and material joint to be achieved in the region of the contour elements 3.1. During the production of the shaped body 2 and the formation of this connection in this region, it is necessary to influence the energy input in such a way that damage to the functional component 1 by heat, i.e. excessive temperatures, can be avoided. The energy input must be limited and influenced in such a way that a maximum temperature, specific to a specifiable functional component 1, at the respective functional component 1 is avoided. The thermal conductivity of the support structure 3 should also be taken into account in this case.

Figure 3A:
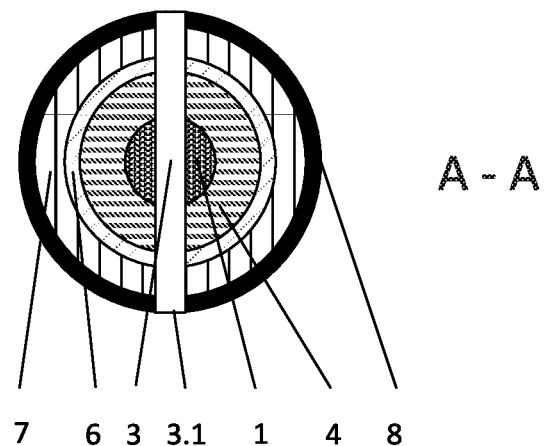
FIG. 3a shows an example of a functional component with a surrounding layer system in a sectional view.

A functional component 1 provided for integration into a shaped body 2 is shown with its plurality of layers in a sectional illustration in FIG. 3a. The functional component 1 is connected to a support structure 3 (not shown), which has contour elements 3.1 on both sides. The functional component 1 is surrounded by a first ceramic layer 4, which is formed from zirconium oxide or aluminum oxide, for example. A further ceramic layer 6, which can advantageously also be formed from ceramics, e.g. bone cement, is formed on this first ceramic layer 4. The layers 4 and 6 both form thermally insulating layers 1.1 (only designated in FIG. 1) and protect the functional component 1 from excessive heat input during the subsequent beam melting. On the further ceramic layer 6 there is the thermally conducting layer 1.2 formed at least as a metallic layer 7, which can be composed of molybdenum. The metallic layer 7, in turn, is surrounded by a sleeve 8 formed as a further thermally conducting layer 1.2 (designated only in FIG. 1) and composed of titanium, which is open at the two ends from which the contour elements 3.1 project. Titanium has been chosen in this example because the shaped body 2 into which the composite comprising the functional component 1 and the support structure 3 is to be integrated is likewise composed of titanium.

All the layers, which are present, on the one hand, for thermal insulation and, on the other hand, for better heat distribution or heat storage, can be formed by means of thermal spraying, in particular plasma spraying. Thus, to form a thermally conducting layer 1.2, for example, a heat-distributing metallic layer 7 composed of molybdenum having a layer thickness in a range of from 50 µm to 200 µm can be applied. Argon or some other suitable inert gas can preferably be used as a protective and cooling gas. In this case, a vacuum would not be absolutely necessarily for thermal spraying. The cooling gas could also be nitrogen. However, the thermal spraying as a thermal coating method could also be carried out under vacuum conditions.

Figure 3B:
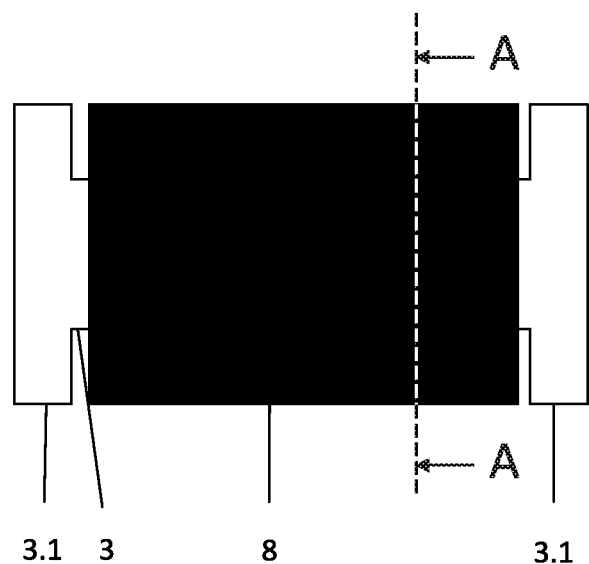
FIG. 3b shows a composite of the functional component with the support structure in side view.
Figure 3C:
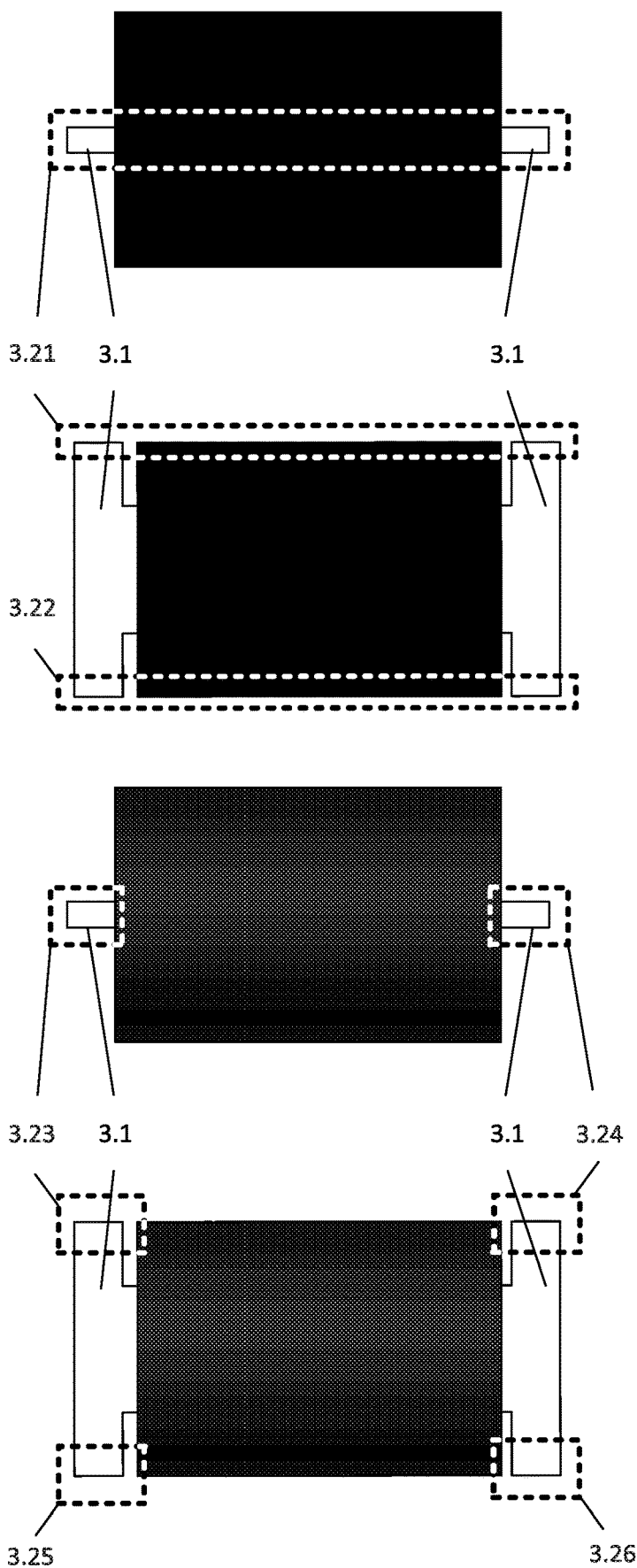
FIG. 3c shows possible beam melting zones.
Figure 3D:
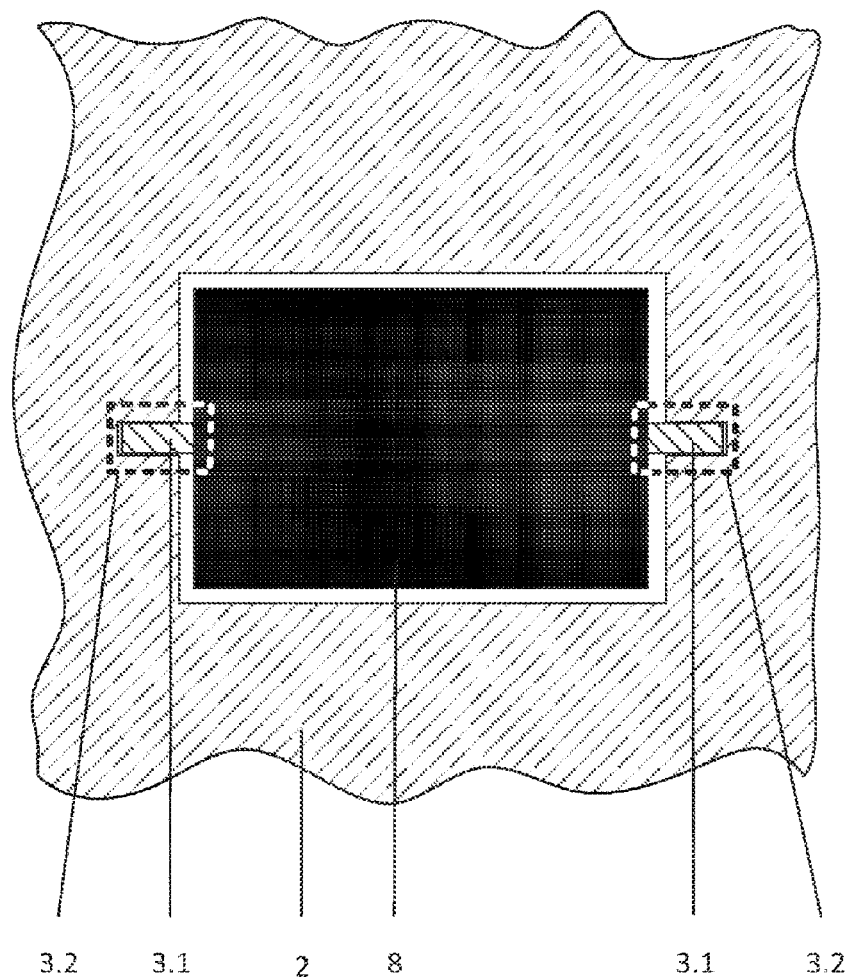
FIG. 3d shows a functional component with a support structure, inserted into a shaped body, as a detail.

In FIG. 3b, the functional component 1 shown in FIG. 3a is shown with its contour elements 3.1 of the support structure 3 in a side view. In FIG. 3c, possible variants of the beam melting zones 3.21 to 3.26 for positive connection to the contour elements 3.1 are shown as particular embodiments of beam melting zones 3.2 (as designated in FIG. 1), wherein two variants each are illustrated in plan view and side view (a first variant having beam melting zones 3.21 and 3.22 and a second variant showing four separated beam melting zones 3.23, 3.24. 3.25, and 3.26). FIG. 3d shows the functional component 1 inserted into the shaped body 2, wherein only the sleeve 8 and the contour elements 3.1 in the beam melting zones 3.2 are illustrated.

FIGS. 4a-d show several examples, each in two views (the left ones of which being cross-sectional views of a plane A-A identified in the side views on the right side), in which a functional component 1 is surrounded by an outer ceramic layer 4 in the region between the outward-projecting contour elements 3.1 of the support structure 3.

All the layers, which are present, on the one hand, for thermal insulation and, on the other hand, for better heat distribution or heat storage, can be formed by means of thermal spraying, in particular plasma spraying. Thus, for example, a heat-distributing metallic layer 7 composed of molybdenum having a layer thickness in a range of from 50 µm to 200 µm can be applied. Argon or some other suitable inert gas can preferably be used as a protective and cooling gas. In this case, a vacuum would not be absolutely necessarily for thermal spraying. The cooling gas could also be nitrogen. However, the thermal spraying as a thermal coating method could also be carried out under vacuum conditions.

In FIG. 3b, the functional component 1 shown in FIG. 3a is shown with its contour elements 3.1 of the support structure 3 in a side view. In FIG. 3c, the various possible beam melting zones 3.2 for positive connection to the contour elements 3.1 are shown (two variants are illustrated in plan view and side view). FIG. 3d shows the functional component 1 inserted into the shaped body 2, wherein only the sleeve 8 and the contour elements 3.1 in the beam melting zones 3.2 are illustrated.

FIGS. 4a-d show several examples, each in two views, in which a functional component 1 is surrounded by an outer ceramic layer 4 in the region between the outward-projecting contour elements 3.1 of the support structure 3.

Figure 4A:
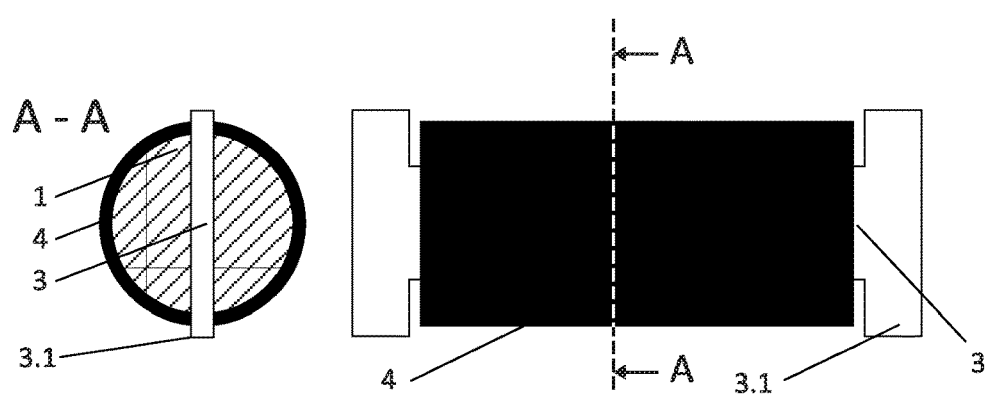
FIG. 4a shows two views of a support structure with contour elements.
Figure 4B:
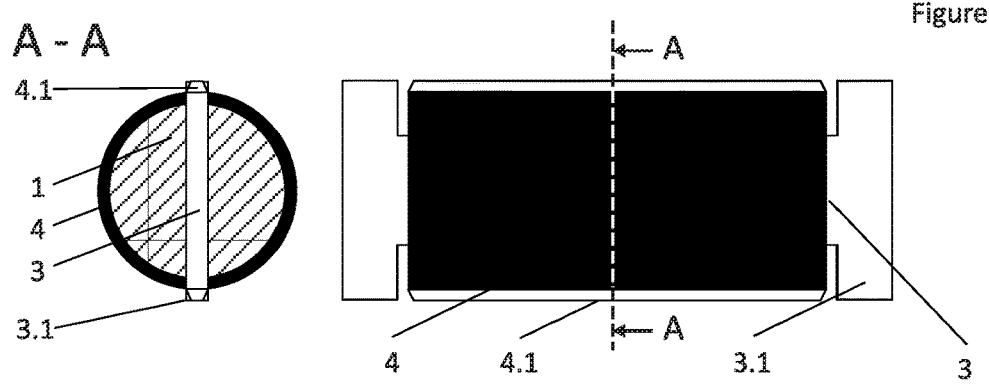
FIGS. 4b-d each show two views of raised portions (in the form of points or linear, arranged axially or radially) for the positive and/or material connection.
Figure 4C:
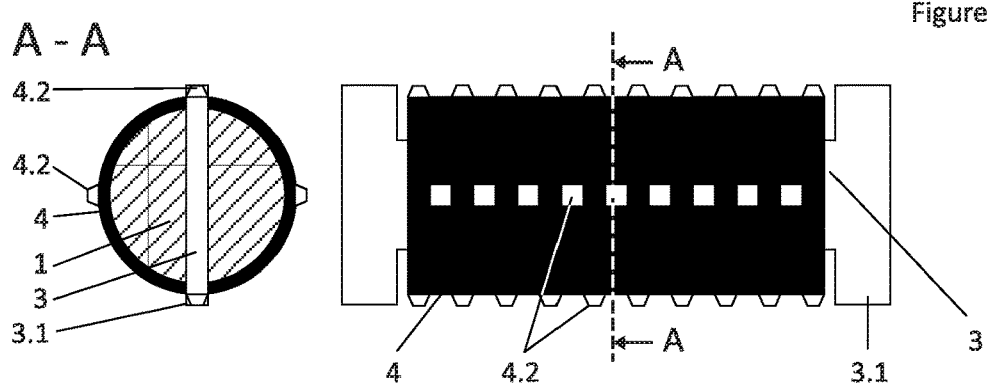
Figure 4D:
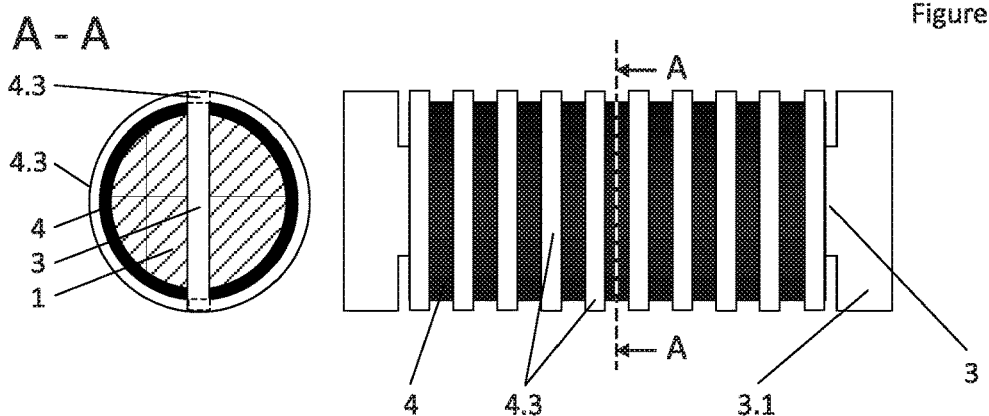

In FIG. 4a, the ceramic layer 4 is a simple hollow cylinder. The example shown in FIG. 4b differs from the example according to FIG. 4a in that two longitudinal bosses 4.1 have been applied to the ceramic layer 4 over the entire length. According to FIG. 4b, these longitudinal bosses 4.1 lie precisely between the contour elements 3.1, although this does not have to be compulsory. In further embodiments, it is also possible for more than two longitudinal bosses 4.1 to be arranged in a manner distributed over the circumference of the ceramic layer 4. In the example shown in FIG. 4c, individual bosses 42 are arranged at discrete intervals over the entire surface of the ceramic layer 4. In FIG. 4d, a plurality of radial bosses 4.3 are arranged in a manner distributed in a ring shape over the entire surface of the ceramic layer 4. All the bosses 4.1, 4.2, 4.3 serve for better material integration with respect to the shaped body 2 and simultaneously perform the function of spacing when a thermally insulating space is deliberately incorporated between the ceramic layer 4 and the shaped body 2 in the further procedure. In cross section, the bosses 4.1, 4.2, 4.3 are preferably trapezoidal since, in this way, an optimum material connection to the shaped body 2 can be produced. Moreover, an arched overlay from boss to boss can thus be achieved in an optimum manner in the region of beam melting zones 3.2. Depending on the application, the bosses 4.1, 4.2, 4.3 can advantageously be composed of ceramics or metal. It is thereby possible to implement spacing and melt-bonding functions.

Figure 5:
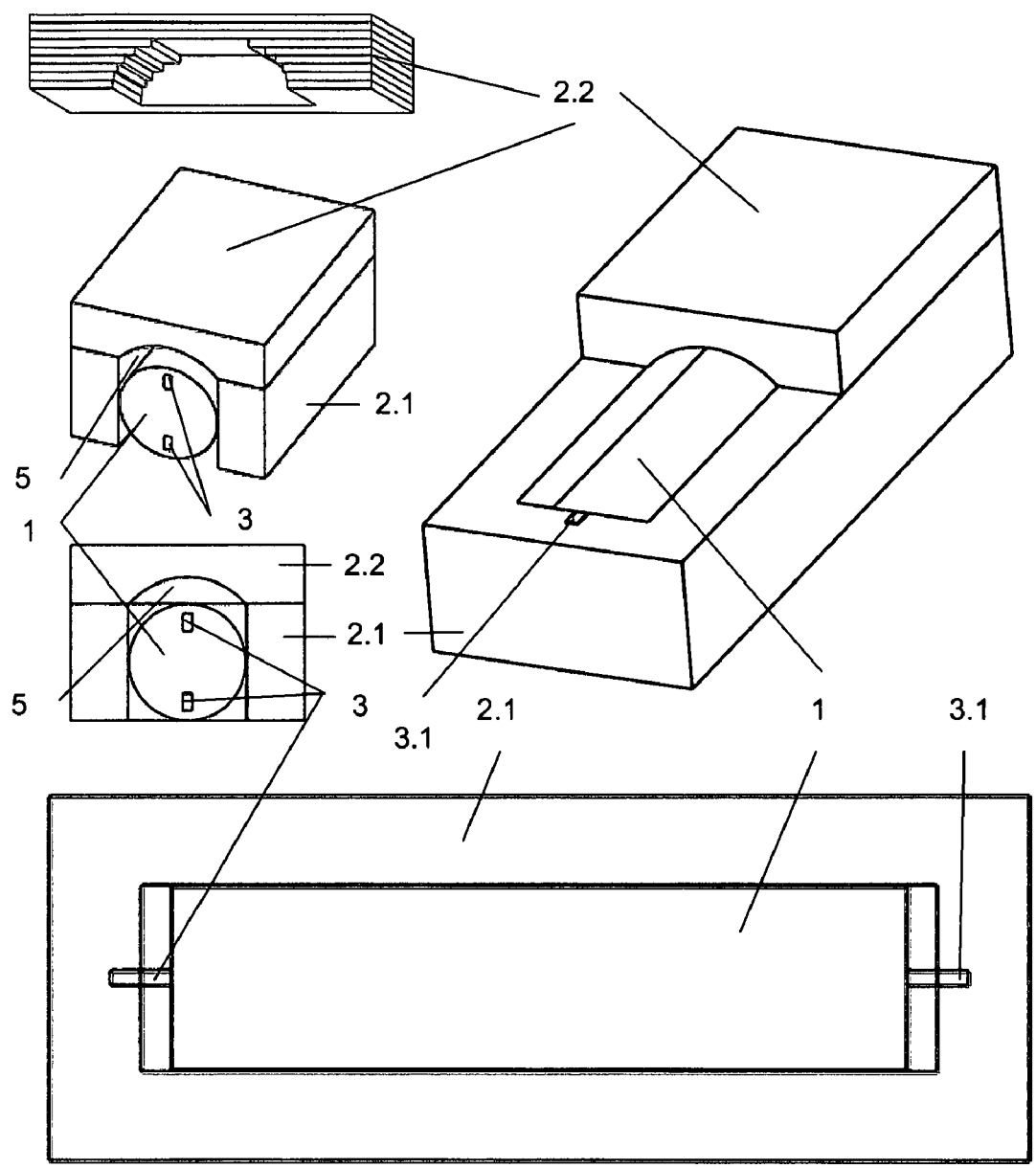
FIG. 5 shows an example in which a functional component has been surrounded by an arch arc of a shaped body, in several views.

FIG. 5 shows, in a number of illustrations, an example in which a functional component 1 has been inserted into a partial body 2.1 that has already been pre-produced. A further partial body 2.2 is produced generatively above this from the same material as the first partial body 2.1 by layered beam melting and thus surrounds the functional component 1. In this example, the functional component 1 with the support structure 3 (not shown) and all its layers (likewise not shown specifically) is inserted flush into the partial body 2.1, with the result that the partial body 2.2 covers over the functional component 1 in an arch-shaped manner. According to FIG. 5, a cavity 5 remains between the outer surface of the functional component 1 and the partial body 2.2. By means of this cavity 5, thermal insulation can be achieved, with the result that heat reaches the functional component 1 with a reduced temperature or not at all during the generative production of the partial body 2.2. The cavity 5 can also be filled with unmelted powder. In principle, the shaped body 2 can be built up generatively in a single session, i.e. first the first partial body 2.1 with simultaneous incorporation of the functional component 1 with its contour elements 3.1 or bosses 4.1, 4.2, 4.3 and, immediately afterward, the further buildup of the partial bodies 2.2, with the result that the shaped body 2 is generated in a single beam melting process. The positive and material connection of the support structure 3 and the shaped body 2 can be formed as in the examples shown in FIGS. 1 and 2.

Figure 6:
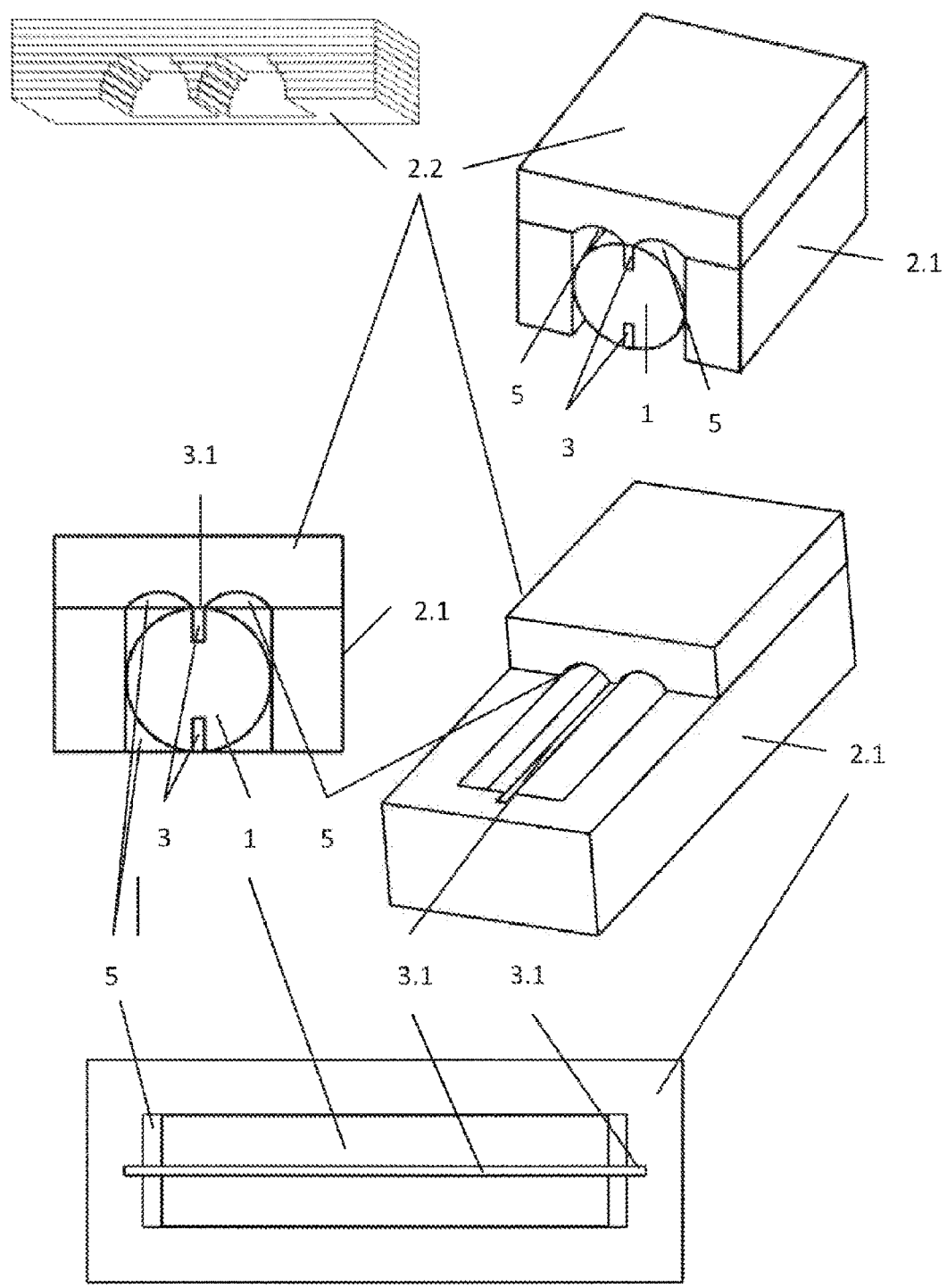
FIG. 6 shows an example in which a functional component has been surrounded by two arch arcs of a shaped body, in several views.

The example shown in FIG. 6 differs from the example according to FIG. 5 in that two arch arcs are formed on the partial body 2.2, wherein the web between the two arch arcs can be used for at least material connection to the support structure 3. In this regard, see also FIG. 3c, the first two depictions, in which the beam melting zones 3.2 are shown. A variant (not shown) according to FIG. 6 can be obtained in an analogous way by constructing the web of the arch arcs by means of a material connection with an arranged longitudinal boss 4.1.

Figure 7A:
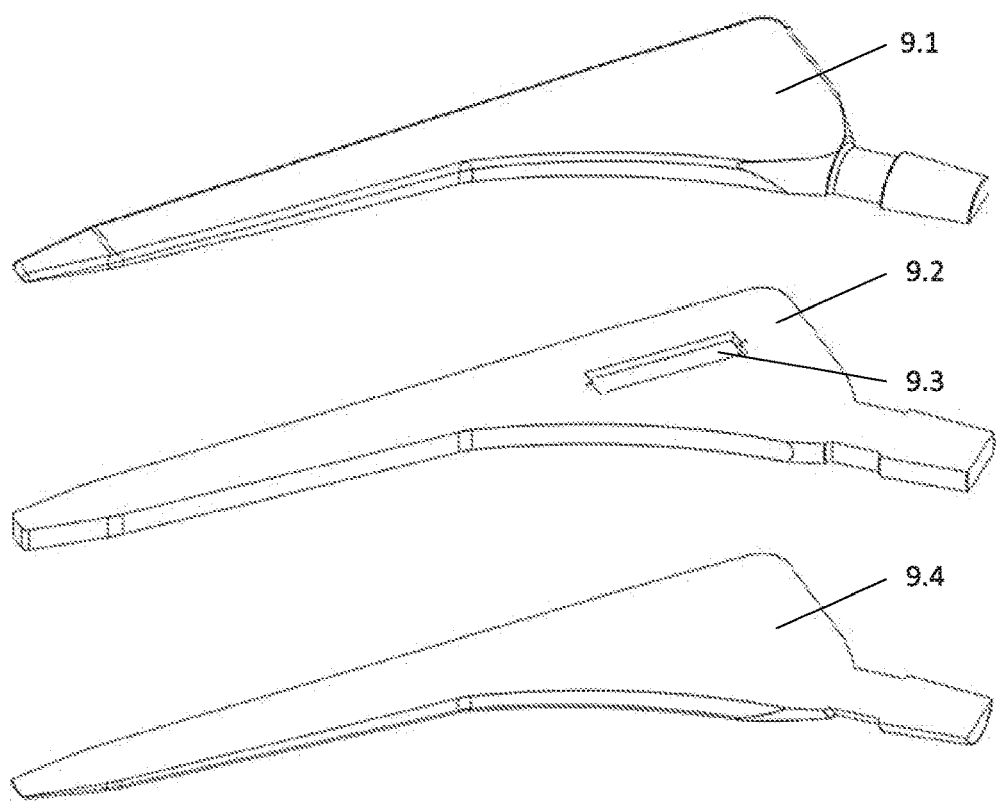
FIG. 7a shows an endoprosthesis as a three-part embodiment.

FIGS. 7a and b show an endoprosthesis as an example of a shaped body 2 into which a functional component 1 with support structure 3 can be integrated. In this case, the endoprosthesis can likewise be produced generatively by beam melting. The endoprosthesis can be produced from titanium or a titanium alloy or from a cobalt-chromium alloy.

Figure 7B:
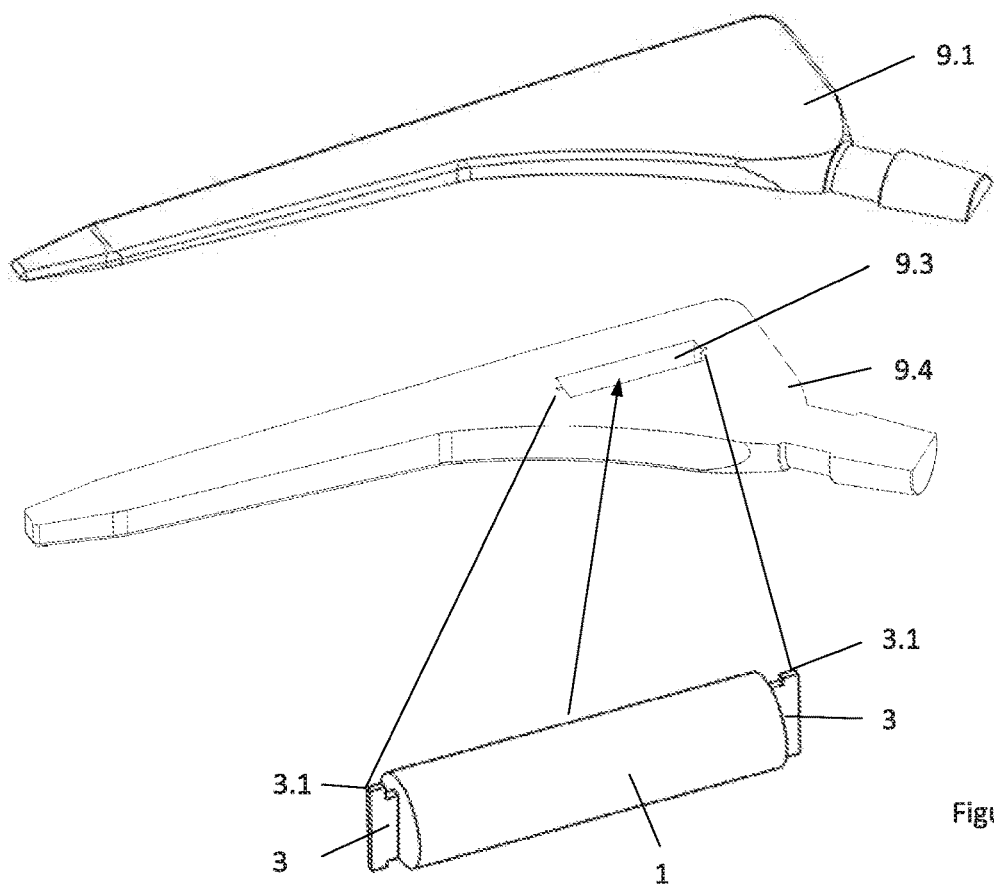
FIG. 7b shows an endoprosthesis as a two-part embodiment.

As is evident from FIG. 7a, the endoprosthesis can be produced generatively in several stages. As shown by the central image, there initially remains in the central part 9.2 an aperture 9.3, into which the functional component 1 with its support structure 3 and the contour elements 3.1 can be inserted and materially connected (not shown in FIG. 7a). The upper part 9.1 is then built up on the central part 9.2 by means of beam melting, and the composite produced from the central part 9.2 and the upper part 9.1 is rotated through 180° and then the lower part 9.4 is built up in a materially bonded way on the composite comprising the central part 9.2 and the upper part 9.1 by means of beam melting. Between the individual buildup steps, the respective partial bodies and composite bodies can also be subjected to conventional machining steps, e.g. grinding. The endoprosthesis produced in this way thus comprises a monolithic shaped body 2 completely surrounding the functional component 1, wherein the upper part 9.1, the central part 9.2 and the lower part 9.4 are as it were materially fused at their boundary surfaces by means of the selected production process. A mechanical, nonthermal post-compaction of the endoprosthesis with the integrated functional component 1 can follow. This is possible, for example, by means of massive cold forming around a layer or material zone with optimum force-absorbing properties, which protects the functional component 1 from excessive mechanical deformation. This aftertreatment can be carried out as a whole or, alternatively, only selectively in partial regions of the endoprosthesis. In this way, the endoprosthesis can be compacted in such a way to ensure a necessary strength, stiffness and stability, after the integration of the functional component 1 and the finishing of additive production and further optionally following joining processes, that the functional component 1 is not deformed in such a way as to impair its functioning. In this case, a locally defined compaction in certain regions of the endoprosthesis, e.g. at a defined distance from the connection interface, is also advantageously possible. By means of the individual mechanical properties of the separate volumes, it is possible to adjust material properties spatially, thus enabling load bearing regions to be passed around the functional component region so as to absorb force without impairing the overall stability of the shaped body 2 and the functioning of the functional component 1. FIG. 7b illustrates a variant, wherein the shaped body 2 comprises a modified lower part 9.4 and an upper part 9.1 identical to FIG. 7a. In contrast to FIG. 7a, no separate central part 9.2 having an aperture 9.3 is produced. Here, the lower part 9.4 is built up with an aperture 9.3 up to the same height compared to the central part 9.2 in FIG. 7a. The aperture 9.3 is configured so as to be open only toward the top, thus allowing the functional component 1 to be inserted with a positive fit into the aperture 9.3, wherein nonpositive and material integration of the support structure 3 of the functional component 1 with the lower part 9.4 takes place. Finally, there follows the building up of the upper part 9.1 on the lower part 9.4 with a materially integrated functional component 1.

Figure 8:
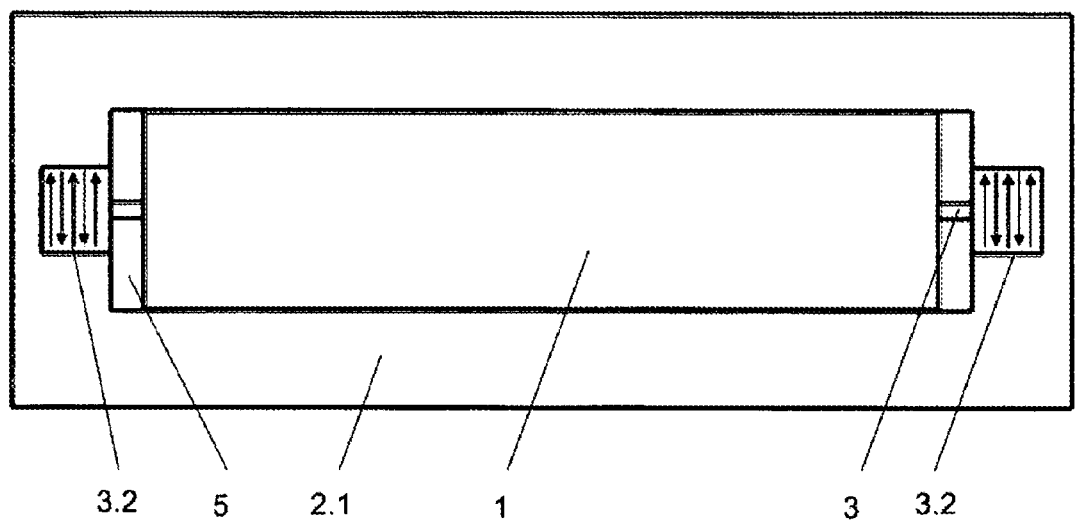
FIG. 8 shows a schematic illustration of the feed motion of an energy beam used for beam melting in the beam melting zone (region of connection of the contour element of the functional component and the shaped body)

FIG. 8 is intended to illustrate how the feed motion of a focal spot of an energy beam can expediently take place in the region of the beam melting zone 3.2 in order to connect the contour element 3.1 materially to the partial body 2.1. There is the possibility in this way of carrying out the irradiation in tracks with an alternating opposed direction of the feed motion of the focal spot in all the layers of the beam melting zone 3.2. As an alternative, a certain specifiable number, e.g. ten layers, which are formed directly above the contour elements 3.1, can also preferably be irradiated in this way and, following this, irradiation can then be carried out in an arbitrary way. In general, however, exceeding of the specific maximum temperature at the functional component 1 due to thermal conduction via the support structure 3 should be avoided.

Figure 9:
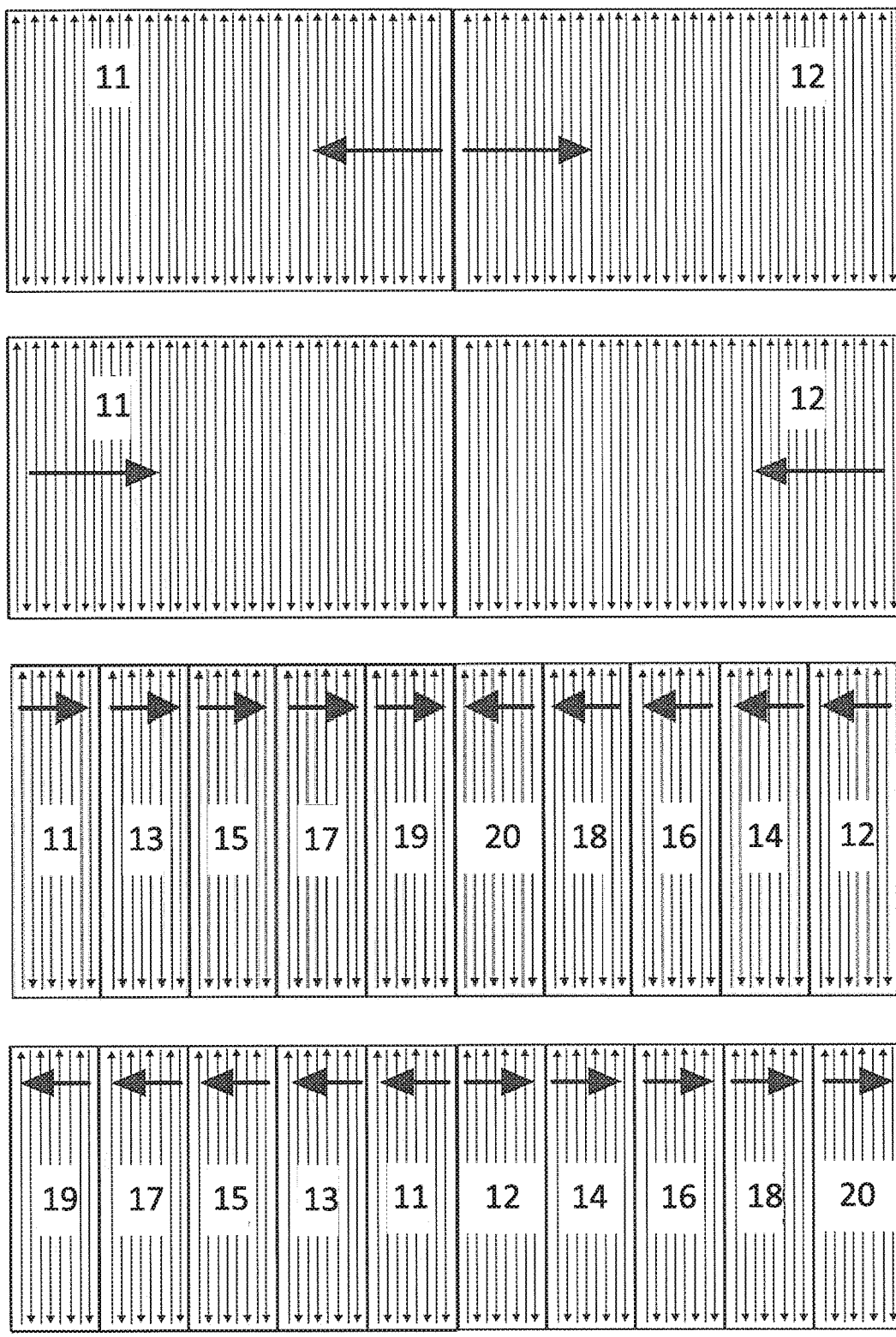
FIG. 9 shows schematic illustrations of irradiation patterns in the production of a shaped body.

FIG. 9 is intended to illustrate how the feed motion of a focal spot of an energy beam can be chosen as an irradiation pattern when layers above a functional component 1 are irradiated and a closed shaped body 2 is produced around the respective functional component 1 by beam melting. The numbers 1 to 10 are used to indicate the respective sequence of the irradiation of segments of the respective layers, and the arrows are used to indicate the direction of the feed motion of the focal spot.

Figure 10:
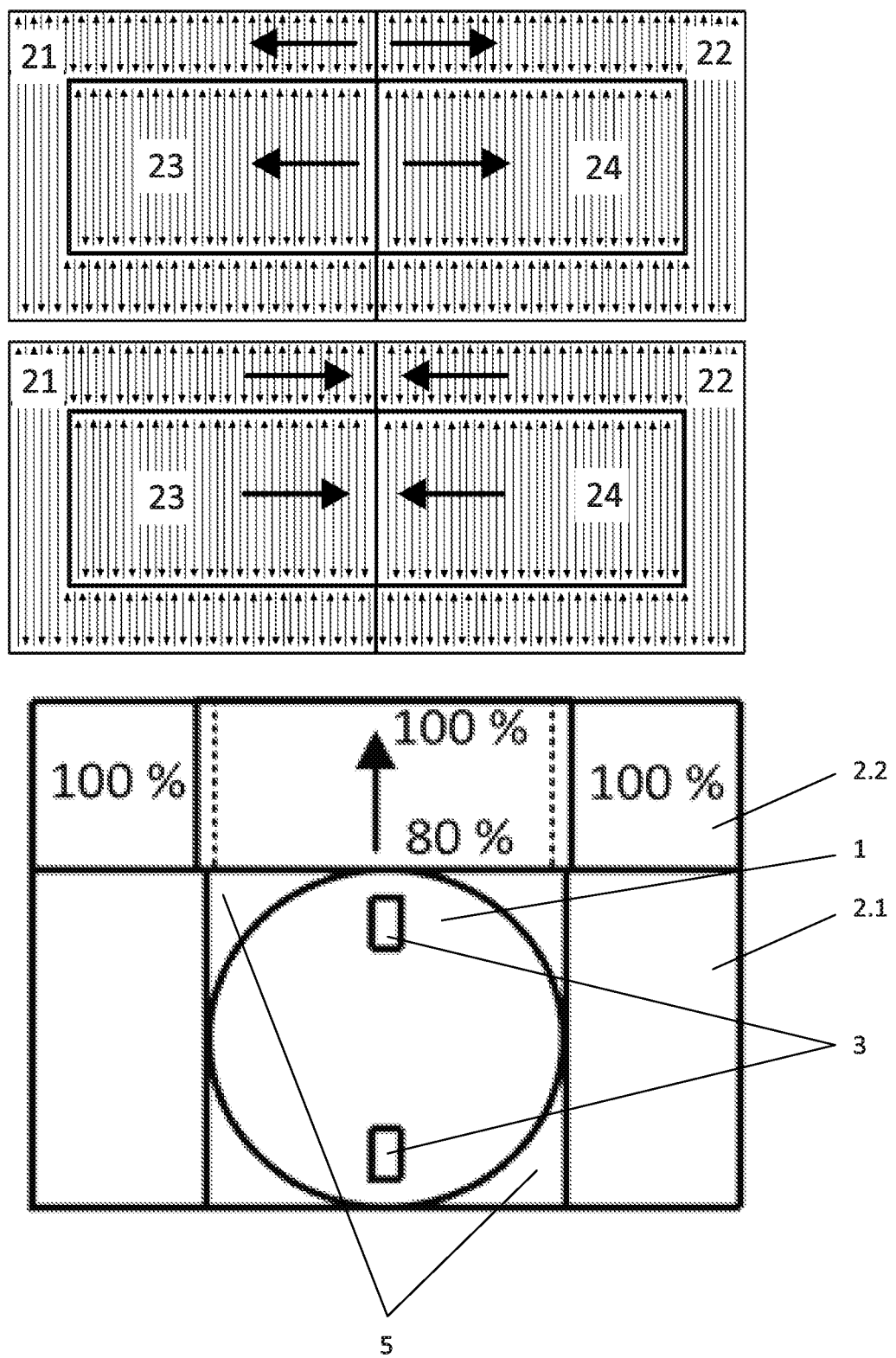
FIG. 10 shows possible irradiation patterns of a moving energy beam with energy input that is variable with respect to location/time during the formation of covering layers over a functional component.

FIG. 10 is intended to illustrate how an energy input reduced to 80% can be achieved during beam melting in regions 13 and 14 which are close to a functional component 1 or thermally sensitive parts or regions of a functional component 1 and/or which are particularly at risk from thermal conduction. In this case, a distance from the surface of the functional component 1 at which the specific maximum temperature due to thermal conduction at the functional component 1 is avoided should be maintained. It becomes apparent that the partial body 2.2 can be produced with a 100% energy input in regions 11 and 12 which, although arranged above the functional component 1, are arranged adjacent to or even at a distance from the functional component 1. In contrast, those regions 13 and 14 of the partial body 2.2 which are arranged immediately above the functional component 1 are produced with a reduced energy input of, in this case, just 80% maximum, which can be adjusted back to 100% with increasing distance. Moreover, the reduction of the energy input to various levels can also advantageously take place within a layer.

In the above images in FIG. 10, alternatively preferred directions of the feed motion of a moving focal spot of an energy beam in certain regions are illustrated by arrows in a plan view. In regions 11 and 12, a full 100% energy input can take place, whereas the energy input should be reduced to 80%, at least in the vicinity of the functional component 1, in regions 13 and 14.

Figure 11:
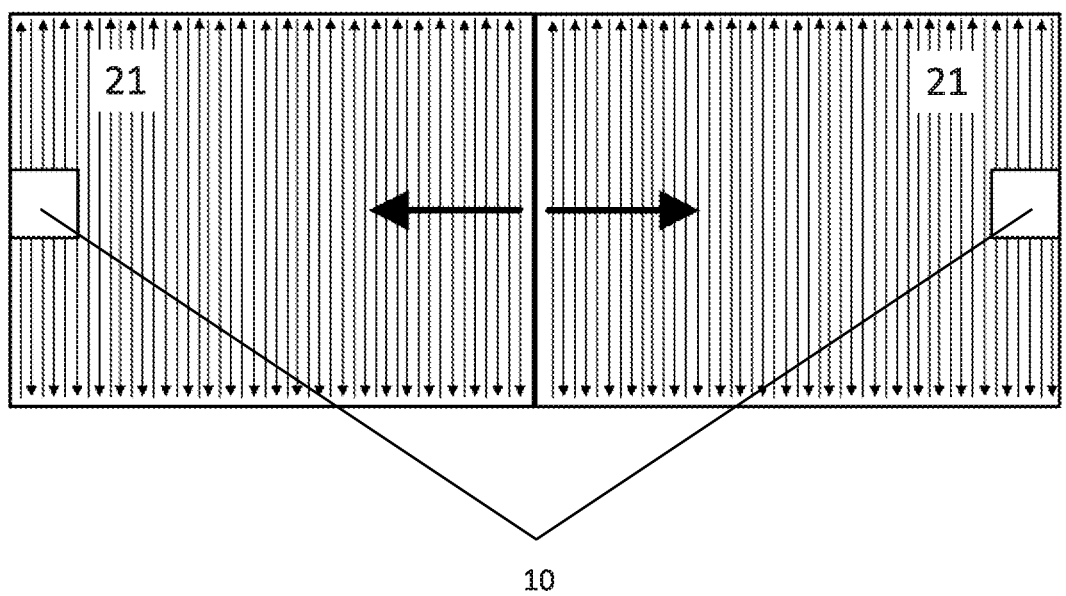
FIG. 11 shows further possibilities of radiation with an energy beam in a manner which is variable with respect to location/time during the formation of covering layers above a functional-component contour element that has already been inserted into the shaped body.

FIG. 11 is intended to illustrate that, during the production of partial bodies 2.1 in regions 10 which are arranged above and/or below a positive and material connection formed or to be formed between contour elements 3.1 and shaped body 2, the heat input can be carried out by means of a different feed motion of a focal spot of an energy beam to that in regions 11 or 12.

During the production of a composite body by means of beam melting, laser powers in a range between 100 W-2000 W and feed rates of the focal spot of a laser beam in the range of 500 mm/s-5000 mm/s can be used. Layer thicknesses in a range of 20 µm-200 µm of individual powder layers which are applied successively and by means of which a locally defined generative buildup takes place should be maintained. The distance between adjacently formed melting tracks, in each case from center to center of these melting tracks, is referred to as the hatch spacing and should be 50 µm to 500 µm. The volume energy densities should be kept in a range of 10 $J/mm^3$-200 $J/lmm^3$ to enable corresponding power densities in the focal spot to be achieved during the melting of the respective powder.

Thus, for example, the material TiAl6V4 can be processed with a laser power of 100 W, a feed rate of the focal spot of a laser beam of 600 mm/s while maintaining a powder layer thickness of in each case 30 µm, a hatch spacing of 105 µm and a volume energy density of 53 $J/mm^3$ if a 100% energy input is to be achieved in accordance with the example shown in FIG. 10.

If a freely vibrating functional component 1 is not necessary or not advantageous in the case of an actuator-sensor-converter variant, e.g. in the case of a thermoactuator as a functional component 1 for the thermal or thermoelectric or electrochemical activation of further agglomerated shape memory actuators, the functional component 1 can or should also be connected or attached positively and materially at its surface to the surrounding shaped body 2. In such an embodiment, the ceramically sheathed functional component 1 is sheathed with a titanium layer materially identical to the shaped body 2, which can then be melted with the materially identical titanium alloy of the shaped body 2 and connected thereto by means of beam melting. In order to avoid unwanted titanium oxide and/or nitride formation during this process, which prevent or comprehensively jeopardize the positive and material connection because of a lack of compatibility, the thermal spraying process should take place under a vacuum.

Alternatively, the ceramically sheathed functional component 1 can be thermally spray-coated with a defined rough titanium layer with a thickness of up to 150 µm and can then be inserted into a sleeve 8 of an identical material or alloy already produced additively beforehand, in particular titanium or a titanium alloy, which may have been thermally aftertreated and compacted in advance. An optimum material, positive and/or nonpositive connection during the subsequent integrating beam melting process would then also be possible without vacuum spraying. For production and assembly reasons, the sleeve 8 can also preferably be of longitudinally slotted design.

In order to protect the thermally sensitive, ceramically sheathed functional component 1 (actuator, sensor and/or some other converter element) during thermal spraying, operational and process management should also be adapted accordingly. If, for example, a maximum temperature of 120° C. is to be complied with in the region of or directly at the functional component 1, this can be influenced by means of the following spray parameters and cooling conditions.

The powder feed rate per spray cycle is reduced or increased during the multiple spraying in a plurality of individual layers until a closed, thermally insulating layer or thermal layer has been formed. During the rotary spraying process, this would be spraying with layer thicknesses in a range of 10 µm-50 µm. In general, three spraying passes are required to form a closed layer. The procedure adopted can be such that two spraying passes are carried out at a low powder feed rate. A holding time is then observed until a temperature reduction to a temperature in a range of from 30° C. to 40° C. has been achieved. After this temperature has been achieved, a further spraying pass is carried out at a higher powder feed rate, by means of which the closed layer has been formed. After this, the temperature is lowered again to a temperature in a range of from 30° C. to 40° C. before a further layer is applied by thermal spraying or a further machining step, during which there can be heating, is carried out.

There is the possibility of carrying out stress-reducing warming, e.g. to 50° C., of the functional component 1 together with one or more ceramic layers formed thereon before subsequent spray coating. The briefly acting temperature gradient during spray coating reaches a temperature below 60° C. to 70° C., i.e. a temperature <120° C. in total (absolute temperature), in the region of the functional component 1.

An inert protective gas should be fed in orthogonally to the spraying direction and, in the process, should flow over a region of at least similar size which the jet influences during thermal spraying. The protective gas flow can be influenced in accordance with the temperatures occurring, and the volume flow can be increased accordingly during heating. Protective gas can be fed in via at least one nozzle at a pressure in a range of from 5 to 6 bar at 40 to 50 standard cubic meters per hour. It is also advantageously possible for protective gas to be fed in from different directions via two nozzles.

If a nonpositive connection is also necessary for a gradient transfer of energy in addition to the positive and material connection between the functional component 1 and the surrounding shaped body 2, this surface of the functional component 1, apart from the connection interface, should not be connected positively and materially to the shaped body 2 in the case of an acoustic converter, for example. In this case, for example, a temperature-distributing metallic layer 7 with a thickness of 50 µm to 200 µm would be sprayed onto the ceramically encapsulated subassembly of the functional component 1 by means of thermal spraying after a thermoinsulating ceramic oxide layer 4.

LIST OF REFERENCE SIGNS

1 functional component
1.1 thermally insulating layer
1.2 thermally conductive layer 2 shaped body
2.1 partial body (lower body, open for integration/embedding)
2.2 partial body (upper body, for closing off after integration/embedding)
3 support structure
3.1 contour element
3.2 beam melting zone
3.21-3.26 variants of beam melting zone 3.2
4 ceramic layer
4.1 longitudinal boss
4.2 individual boss
4.3 radial boss
5 cavity
6 further ceramic layer
7 metallic layer
8 sleeve
9.1 upper part
9.2 central part
9.3 aperture
9.4 lower part
10 region
11 to 24 represent the respective sequence of irradiation of segments

What is claimed is:

1. A composite body, wherein the composite body comprises at least one functional component and a shaped body and wherein:
the at least one functional component is arranged so as to be connected to a metallic or ceramic support structure, which metallic or ceramic support structure comprises at least one contour element,
the at least one functional component is surrounded at least in some region or regions by at least one thermally insulating layer of a ceramic material and at least one thermally conductive layer lying above the at least one thermally insulating layer of ceramic material, which at least one thermally conductive layer is composed of a thermally conductive metal, metal alloy or metal oxide, and
the shaped body is produced generatively by beam melting of a metal powder and completely surrounds the at least one functional component and the support structure comprising the at least one contour element, at least one of the at least one contour elements being materially connected to the shaped body by a beam melting zone.

2. The composite body of claim 1, wherein the support structure comprises at least one outwardly projecting contour element which is arranged so as to reach into the beam melting zone of the shaped body.

3. The composite body of claim 1, wherein the support structure is provided at least in some region or regions with a metallic coating.

4. The composite body of claim 1, wherein the at least one functional component is an actuator and/or a sensor and/or an energy converter element.

5. The composite body of claim 1, wherein the thermally conductive layer has a higher melting temperature than the shaped body.

6. The composite body of claim 2, wherein at least in the regions which adjoin the beam melting zone, the at least one outwardly projecting contour element is formed from the metal of the shaped body or an oxide of a material from which the shaped body is formed, or is formed from a metal or a metal alloy which can be connected materially to the material of the shaped body.

7. The composite body of claim 6, wherein the at least one functional component and/or the support structure has different physical and/or chemical properties, from the shaped body.

8. The composite body of claim 2, wherein the at least one outwardly projecting contour element and the shaped body have adapted microstructures at their boundary surfaces in the beam melting zone.

9. The composite body of claim 1, wherein the thermally conductive layer is a sleeve.

10. The composite body of claim 9, wherein a connection between the sleeve and the shaped body is a material connection.

11. The composite body of claim 1, wherein the at least one functional component is connected positively, non-positively and/or materially to the support structure via thermally insulating layers.

12. The composite body of claim 1, wherein the composite body further comprises a partial body in which the support structure, together with the at least one functional component thereof, is arranged and via which the at least one contour element is materially connected, the partial body being covered over in a manner of an arch with a further partial body, and the partial body and the further partial body being materially connected.

13. The composite body of claim 1, wherein there are bosses between an outer peripheral surface of the at least one functional component and an adjoining inner wall of the shaped body, thus forming a space which is not melted into a material joint and which has thermally insulating properties.

14. A method for producing the composite body of claim 1, wherein the method comprises
connecting the at least one functional component to the metallic or ceramic support structure,
thereafter providing the at least one functional component at least in some region or regions with the at least one thermally insulating surrounding layer composed of a ceramic material by thermal spraying,
thereafter applying the thermally conductive layer composed of a metal or metal oxide or metal alloy on top, likewise by thermal spraying,
thereafter producing generatively and in layers by beam melting a metal powder a partial body comprising at least one beam melting zone and aperture for receiving a unit produced thus far,
thereafter inserting a unit produced thus far positively, non-positively and/or materially into the aperture in the partial body, the support structure being connected materially, by the beam melting zone, to the partial body, indirectly or directly via contour elements and/or via bosses, and
finally, covering over the aperture generatively and in layers with at least one further partial body, likewise by beam melting a metal powder, thus giving rise to a monolithic shaped body according to claim 1.

15. The method of claim 14, wherein an energy beam is operated in such a way and the focal spot thereof moved in such a way during a beam melting process that a maximum temperature specific to a preservation of the functioning of a respective functional component is not exceeded during the production of the shaped body.

16. The method of claim 15, wherein an energy density in a focal spot of the energy beam, a feed rate of the focal spot, a spacing between melting tracks, a respective layer thickness of powder layers and/or an irradiation pattern are influenced in such a way that the specific maximum temperature is not reached at the functional component.

17. The method of claim 14, wherein metal powder applied and/or already melted layers thereunder are preheated before a beam melting of an applied metal powder layer.

18. The method of claim 14, wherein a maximum reduction of an energy input takes place in a vicinity of temperature-sensitive parts of the functional component to preserve a microstructure and functioning, and the reduction of the energy input decreases with increasing distance therefrom.

19. The method of claim 14, wherein the shaped body is produced from a plurality of partial bodies which are produced generatively by beam melting and are connected to one another materially.

20. The method of claim 14, wherein the thermally insulating layer and/or the thermally conductive layer is/are formed by thermal spraying by a plurality of individual layers formed one above the other and, during this process, holding phases for cooling are implemented and/or thermal spraying is carried out under vacuum conditions or by using an inert protective gas.

* * * * *